(12) United States Patent
Young

(10) Patent No.: US 9,271,739 B2
(45) Date of Patent: Mar. 1, 2016

(54) SURGICAL INSTRUMENT AND SYSTEM OF SURGICAL INSTRUMENTS

(75) Inventor: Duncan Young, Leeds (GB)

(73) Assignee: DEPUY (IRELAND), Cork (IE)

( * ) Notice: Subject to any disclaimer, the term of this patent is extended or adjusted under 35 U.S.C. 154(b) by 974 days.

(21) Appl. No.: 13/389,199

(22) PCT Filed: Aug. 3, 2010

(86) PCT No.: PCT/GB2010/051279
§ 371 (c)(1),
(2), (4) Date: Feb. 22, 2012

(87) PCT Pub. No.: WO2011/015863
PCT Pub. Date: Feb. 10, 2011

(65) Prior Publication Data
US 2012/0143199 A1     Jun. 7, 2012

(30) Foreign Application Priority Data
Aug. 6, 2009 (GB) .................................. 0913674.8

(51) Int. Cl.
*A61B 17/15*     (2006.01)
*A61B 17/17*     (2006.01)

(52) U.S. Cl.
CPC ............... *A61B 17/15* (2013.01); *A61B 17/155* (2013.01); *A61B 17/1764* (2013.01)

(58) Field of Classification Search
CPC .... A61B 17/15; A61B 17/151; A61B 17/152; A61B 17/154; A61B 17/155
USPC ....................................................... 606/295
See application file for complete search history.

(56) References Cited

U.S. PATENT DOCUMENTS 3,695,259 A * 10/1972 Yost .............................. 606/288
4,261,350 A * 4/1981 Branemark et al. ........ 606/86 R
4,941,481 A     7/1990 Wagenknecht
(Continued)

FOREIGN PATENT DOCUMENTS

CN     2332372 Y     8/1999
DE     10309493 A1     9/2004
(Continued)

OTHER PUBLICATIONS

PCT International Search Report and Written Opinion PCT/GB2010/051279 dated Nov. 18, 2010.
(Continued)

*Primary Examiner* — Christian Sevilla

(57) ABSTRACT

A surgical instrument, for example a cutting block for use in knee surgery, comprises a mounting surface defining at least one opening for receiving a mounting projection. The mounting surface further defines a blind recess which extends linearly from the at least one opening. The blind recess may extend to an edge of the mounting surface. A system including a surgical instrument and one or more mounting projections is also disclosed. The blind recess can be used as a track to guide a projection to an opening, increasing the area of the instrument that can be used to locate the projection in the correct position. The recess acts as a guide for the projection to enter the opening by providing tactile feedback to guide the projection towards the opening. If the recess also extends to the edge of the instrument, the recess may be visible more easily when the surgeon is installing the instrument providing visual as well as tactile feedback.

20 Claims, 7 Drawing Sheets

(56) References Cited

U.S. PATENT DOCUMENTS

| | | | | |
|---|---|---|---|---|
| 5,053,036 A | * | 10/1991 | Perren et al. | 606/291 |
| 5,129,909 A | | 7/1992 | Sutherland et al. | |
| 5,250,048 A | * | 10/1993 | Gundolf | 606/297 |
| 5,282,803 A | * | 2/1994 | Lackey | 606/80 |
| 5,591,169 A | * | 1/1997 | Benoist | 606/59 |
| 5,683,398 A | | 11/1997 | Carls et al. | |
| 5,733,287 A | * | 3/1998 | Tepic et al. | 606/280 |
| 6,007,537 A | * | 12/1999 | Burkinshaw et al. | 606/66 |
| 6,013,081 A | * | 1/2000 | Burkinshaw et al. | 606/88 |
| 6,159,214 A | | 12/2000 | Michelson | |
| 6,969,393 B2 | | 11/2005 | Pinczewski et al. | |
| 7,527,641 B2 | * | 5/2009 | Suh | 606/289 |
| 7,993,341 B2 | | 8/2011 | Grimm et al. | |
| 8,016,833 B2 | | 9/2011 | Roger et al. | |
| 2005/0182404 A1 | * | 8/2005 | Lauryssen et al. | 606/69 |
| 2006/0058803 A1 | * | 3/2006 | Cuckler et al. | 606/79 |
| 2006/0058806 A1 | | 3/2006 | Collazo | |
| 2006/0212056 A1 | * | 9/2006 | Salvadori et al. | 606/167 |
| 2008/0015602 A1 | | 1/2008 | Axelson | |
| 2009/0087276 A1 | | 4/2009 | Rose | |
| 2009/0149964 A1 | | 6/2009 | May | |

FOREIGN PATENT DOCUMENTS

| | | | |
|---|---|---|---|
| EP | 947169 | A2 | 10/1999 |
| GB | 2445620 | A | 7/2008 |
| JP | 7508203 | A | 9/1995 |
| JP | 0516114 | A5 | 5/2005 |
| JP | 2006130315 | A | 5/2006 |
| WO | 9400056 | | 1/1994 |
| WO | WO 9729697 | A1 | 8/1997 |
| WO | WO 0166021 | A1 | 9/2001 |
| WO | WO 03099144 | | 12/2003 |

OTHER PUBLICATIONS

UK Search Report GB0913674.8 dated Dec. 4, 2009.
Chinese Search Report for Corresponding Chinese Patent App. No. 20100035835.0, Dated Dec. 30, 2013, 2 Pages.
Australian Search Report for Corresponding Australian Patent App. No. 2010280478 Dated Feb. 28, 2014, 3 Pages.
Japanese Search Report for Corresponding Japanese Patent App. No. 2012-523391 Dated Mar. 11, 2014, 6 Pages.
Chinese Search Report for Corresponding Chinese Patent App. No. 201080035835.0, Dated Apr. 9, 2014, 5 Pages.
Australian Search Report for Corresponding Australian Patent App. No. 2014208272 Dated Mar. 6, 2015, 3 Pages.
Japanese Search Report for Japanese Application No. 2014125211 Dated Apr. 13, 2015, 2 Pages.
Australian Search Report for Australian Application No. 2014208272 Dated Aug. 14, 2015, 4 Pages.
European Search Report for EPO Application No. 15167188.01654, Dated Oct. 16, 2015, 4 Pages.

* cited by examiner

SURGICAL INSTRUMENT AND SYSTEM OF SURGICAL INSTRUMENTS

CROSS REFERENCE TO RELATED APPLICATION

This application is a National Stage 35 U.S.C. 371 of International Patent Application PCT/GB2010/051279, filed Aug. 3, 2010.

BACKGROUND OF THE INVENTION

The present invention relates to surgical instruments and in particular to surgical instruments that include openings for engaging projections to hold the surgical instrument in a particular position.

Many surgical instruments require fixing in a known position relative to a patient. One example is a cutting block. Cutting blocks are typically affixed to a patient's bone in a position such that they can guide cutting and resection of the bone surface for receiving an implant.

Existing cutting blocks are mounted to a patient's bone by engaging projections or pins in recesses. In some systems the projections extend from the cutting block and engage holes drilled in the bone. In other systems a fixed reference philosophy is used and the cutting block contains openings or holes that engage projections installed in the bone and which extend from the bone surface.

In a fixed reference philosophy, instrumentation is first used to determine the correct position for the projections on the bone. The projections are then inserted into the bone and used to mount the cutting block and hold it in the correct position relative to the bone by engaging the openings on the cutting block.

If the cutting block is only intended to be provided in one position relative to the projections then one set of openings is provided, with each opening in the set positioned to receive each projection. Alternatively, the cutting block may be mounted in a number of different positions relative to the projections. For example, the surgeon may need to alter the position of the cut slightly from the measured position without having to reposition the projections. In that case the cutting block may include a number of sets of openings for engaging the projections.

Placing the cutting block on the projections is difficult. The projections extend from the bone surface in a direction towards the cutting block. As the surgeon looks at the cutting block and moves it towards the mounting projections, the position of the projections relative to the openings is obscured by the cutting block itself.

To overcome this problem, surgeons may attempt to view the bone surface while placing the cutting block on the pins. However, it can be difficult to position the patient such that this view is available, or it can require unacceptable manipulation of the patient. Even if the surgeon can view the projections, surgical lighting is designed for viewing from the direction the cutting block is installed. It can be difficult to identify the projections and openings accurately against the backdrop of the bright surgical lighting.

To assist in placement of the projections in the openings it is known to provide chamfers on the edges of the holes. These widen the entrance to the hole slightly, assisting alignment of the pins. However, due to design constraints the chamfer can be very small. For example, the space available between adjacent holes may constrain any chamfer so that it is over a radial distance of less than a millimeter. This limits the usefulness of the chamfer.

If the cutting block is placed on more than one projection, for example a pair of projections, it can be difficult to place the cutting block if the projections have not been installed in precisely the correct position. For example, one of the projections may be at a slight angle relative to another of the projections so that they do not align exactly with the openings.

Accordingly, the present invention provides a recess or slot which extends linearly from an opening for engaging a projection such as a pin. The recess may extend from the opening to the edge of the instrument.

The recess can be used as a track to guide a projection to an opening, increasing the area of the instrument that can be used to locate the projection in the correct position. The recess acts as a guide for the projection to enter the opening by providing tactile feedback to guide the projection towards the opening. If the recess also extends to the edge of the instrument, the recess may be visible more easily when the surgeon is installing the instrument providing visual as well as tactile feedback.

BRIEF SUMMARY OF THE INVENTION

According to the first aspect of the present invention, there is provided a surgical instrument comprising a mounting surface, wherein the mounting surface defines at least one opening for receiving a mounting projection; and wherein the mounting surface further defines a blind recess which extends linearly from the at least one opening.

The at least one opening can delimit a through hole or a blind hole. The opening may have a circular cross-section or another cross-section. For example, in some embodiments the opening may be triangular, square or other shapes for engaging corresponding mounting projections with the same cross-section. (Non-circular cross-sections may be useful when an instrument is mounted on a single mounting projection, but orientation of the instrument in relation to the mounting projection is important).

The blind recess is a recess that does not extend through the entire depth of the surgical instrument.

A surgical instrument with these features can be installed more easily on the mounting projection without requiring visibility of the mounting projection as it aligns with the opening. The recess extends linearly unlike the radial extension of a chamfer. This allows it to cover more surface area of the mounting surface so the projection can be engaged more easily. The linear nature of the recess then assists in providing tactile feedback to guide the projection towards the opening. The mounting projection can remain in the recess throughout movement of the instrument to align the mounting projection with the opening, so that recess provides tactile feedback to the surgeon as the mounting projection is moved towards the opening. Thus, the surgical instrument according to the present invention can be placed more easily on a mounting projection.

The surgical instrument may further comprise a first side surface adjacent the mounting surface and the blind recess may extend to a first edge of the mounting surface such that the recess extends into the first side surface. The surgeon can then generally align the mounting projection with the blind recess while the instrument is tilted slightly, so that the section of the recess which extends to the edge of the mounting surface can be seen. The projection may be aligned with the blind recess visually by the extension of the recess to the side surface and the recess itself then acts as a track or guide, guiding the mounting projection towards the opening.

In one embodiment the blind recess has a width which increases in the direction towards the first side surface. For example, this can define a chamfer or funnel shape towards the first side surface. This increases the area of the first side surface in which the mounting projection can be located initially before being guided to the opening, making placement simpler. In embodiments with two or more openings for receiving mounting projections and two or more blind recesses, the increasing width in the direction towards the first side surface can allow the instrument to automatically correct slight differences in the location of the pins. The increasing width will guide all the projections towards the correct position as they move towards the openings.

The blind recess may have a depth which increases in the direction towards the first side surface. This increases the visibility of the blind recess when a surgeon is positioning the instrument. It can allow the blind recess to be optimised so that the area available for receiving a projection is maximised towards the edge without compromising the actual depth of opening provided for the projection. This may be important because in order to ensure accurate alignment the opening may have to extend over sufficient depth to hold the instrument in the correct position.

It will be noted that the width of the blind recess need not be the same as the width of the opening. For example the blind recess may be slightly narrower than the opening and still guide a projection towards the opening. This may be suitable when design constraints limit the size of the recess that can be formed on the mounting surface.

The blind recess may be generally straight and substantially perpendicular to the first edge of the mounting surface. This also assists aligning the instrument with a mounting projection. A surgeon can see the intersection of the blind recess with the first side surface and, if the blind recess is straight and extends perpendicularly the surgeon can then easily determine the direction of movement in order to engage a mounting projection with an opening, in addition to any tactile feedback that may be provided by the blind recess.

The blind recess may be intersected by other surface features of the surgical instrument, for example by a slot for guiding a cutting instrument. An intersected recess can still guide a mounting projection. It is desirable that an intersection has a size less than the width of the mounting projection so that the mounting projection can be guided through the recess more smoothly.

In one embodiment the mounting surface defines first and second openings for receiving a mounting projection; wherein a first blind recess extends from the first opening and a second blind recess extends from the second opening; wherein both the first and second blind recesses extend to the first edge of the mounting surface such both the first and second blind recesses extend into the first side surface; and wherein the first and second recess are substantially parallel to each other in the plane of the mounting surface.

This embodiment provides first and second openings for corresponding mounting projections. This can be useful when the surgical instrument requires mounting on two projections. For example, orientation of the instrument relative to the mounting projections may be important, or a more secure fitting may be required. In this embodiment, it is particularly advantageous if the blind recess has a width which increases in the direction towards the first side surface. As explained above, this can allow slight misalignment of the mounting projections relative to each other to be corrected by the blind recess as the projections are moved towards openings. For example, if one of the projections has been mounted at a slight angle relative to the other projection, the recess may assist in bending the projection slightly so that it is in the correct position relative to the other projection to correctly engage the openings.

In another embodiment, a second side surface is adjacent the mounting surface and opposite to the first side surface, and wherein the blind recess extends across the entire mounting surface from the first edge to a second edge such that the blind recess extends into both the first and second side surfaces.

In this embodiment the blind recess extends across the entire mounting surface so that it is visible from first and second side surfaces. This embodiment could be used when the surgical instrument could be inserted from different directions, because the blind recess is visible from two different directions by extending into two surfaces. Alternatively, it can also be used when at least two openings are provided in a line. In that case the recess may extend between all the openings allowing a surgeon to align the instrument by sliding it along the projections in the direction of the line formed between the projections.

The mounting surface may define at least first and second openings and the blind recess may extend between the first and second openings.

Optionally, the mounting surface may define at least one further opening for receiving a mounting projection and wherein no blind recess extends from the at least one further opening This can allow for repositioning the surgical instrument slightly relative to the projections if required. A blind recess is not provided for the further opening. Although this may make it more difficult to locate the projection in the further opening, it avoids confusion between openings and may be more suitable depending on the amount of space available on the mounting surface.

The present invention is particularly advantageous when applied to cutting blocks for orthopaedic surgery. For example it may be applied to a cutting block for guiding resection or drilling on the condyles of the knee joint. In that case the cutting block may define slots for bores which pass all the way through the depth of the cutting block for defining anterior and/or posterior chamfers and/or cuts. These slots and bores are not blind recesses because they are formed through the entire depth of the cutting block. However, it will be appreciated that in alternate embodiments the present invention can also be applied to other surgical instruments including, but not limited to: sizing guides, pin pullers, pin inserters, drill towers, notch guides, tibial trials, tibial cutting blocks and femoral cutting blocks.

According to another aspect of the present invention, there is provided a system of surgical instruments comprising a mounting projection and a surgical instrument as described above.

The mounting projection can be anything suitable for mounting the surgical instrument. For example it may be cylindrical or alternatively may have another cross section such as triangular, square, etc. depending on the particular application. In one embodiment the mounting projection may be adapted for insertion into a bone.

BRIEF DESCRIPTION OF THE DRAWINGS

Embodiments of the invention will now be described by way of example only with reference to the accompanying drawings in which like reference numerals denote like parts and in which.

DETAILED DESCRIPTION OF THE INVENTION

FIGS. 1-7 depict different views of a cutting block 2 according to the first embodiment of the invention. In this embodiment the cutting block is for use in knee surgery. It is a four-in-one cutting block, so called because a single cutting block can define four different cuts by guiding a cutting device through slots 4, 6, 8 and 10. In order to allow the cutting block 2 to be positioned on mounting projections or pins (not shown) the cutting block 2 defines a number of openings of through holes. Towards the top of the cutting block 2 three pairs of openings 12, 14, 16 define through holes. Each of the two openings in each pair, 12, 14, 16 are positioned the same distance apart but the pairs of openings 12, 14, 16 are offset slightly from each other. This enables the surgeon to adjust the position of the cutting block relative to the bone slightly in use, without needing to reposition the mounting projections.

Three more pairs of openings 18, 20, 22 are defined towards the bottom of the cutting block 2. As with the three pairs of openings 12, 14, 16, the lower pairs of openings 18, 20, 22 are the same distance apart from each other with each pair offset slightly from an adjacent pair.

Figure 1:
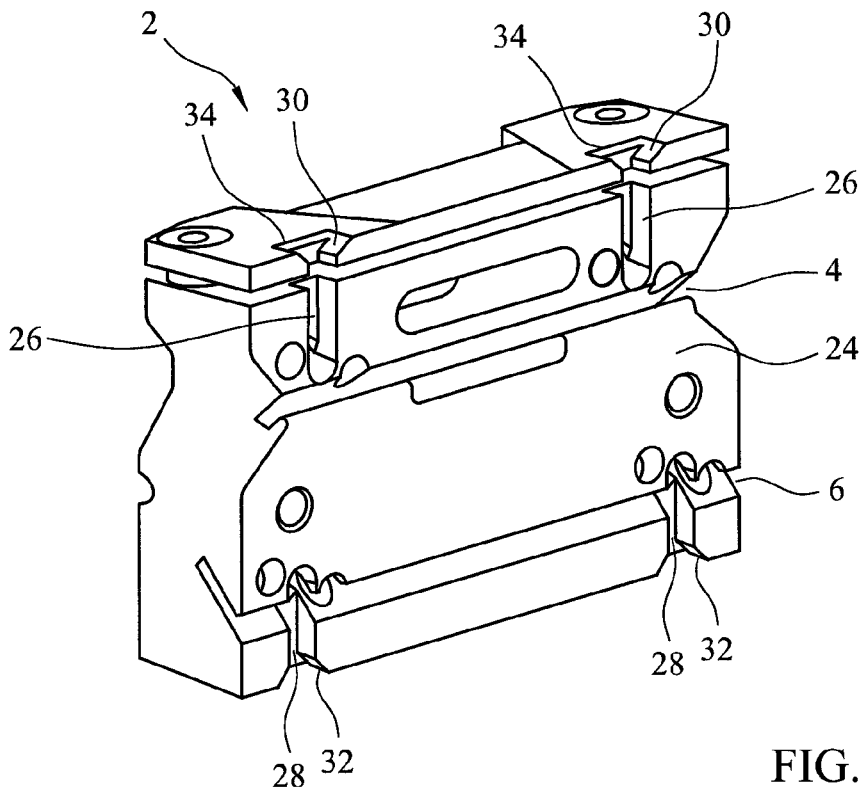
FIG. 1 is an isometric view of a first embodiment of the present invention viewed from the rear.
Figure 6:
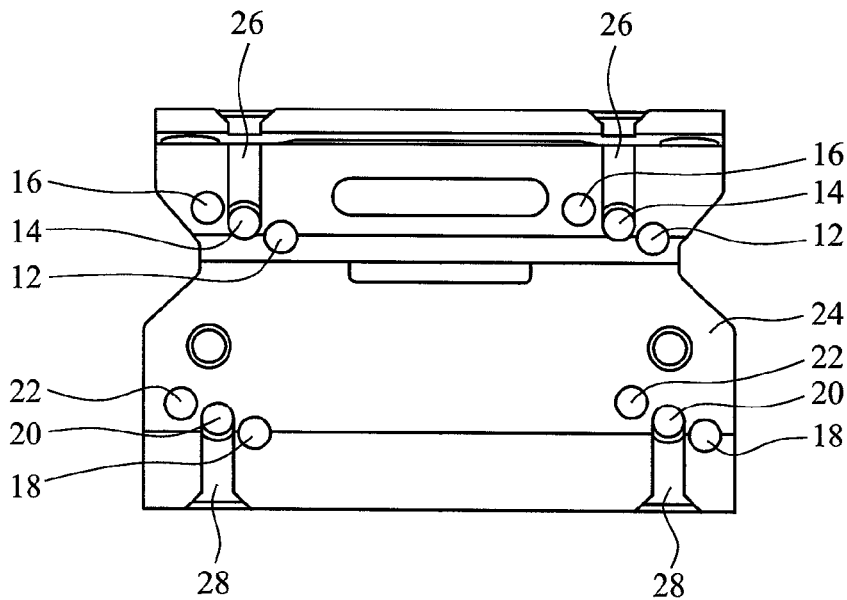
FIG. 6 is a view from the rear of the embodiment of FIG. 1.
Figures 5, 7:
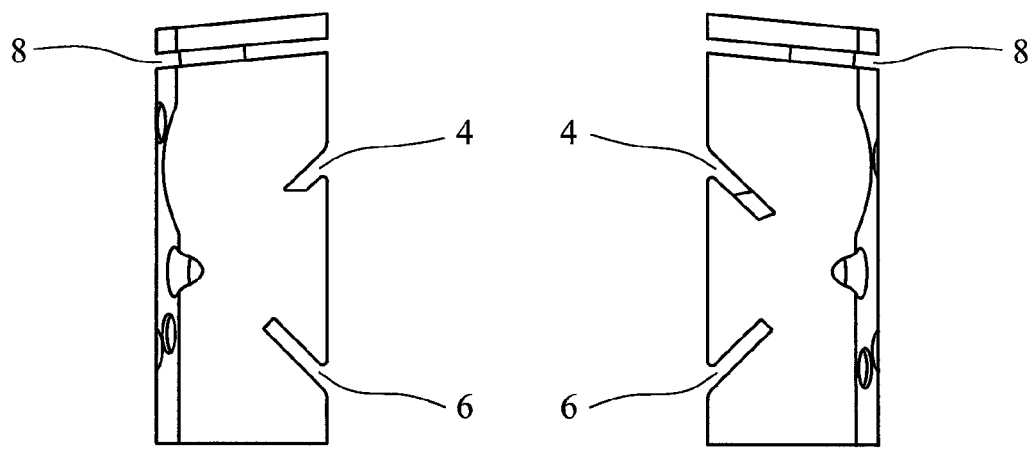
FIG. 5 is a view from the right of the embodiment of FIG. 1.
FIG. 7 is a view from the left of the embodiment of FIG. 1.

As can be seen most clearly in FIGS. 1 and 6 openings 14 towards the top of the cutting block and openings 20 towards the bottom of the cutting block are positioned at the end of a recess formed in a mounting surface 24 of the cutting block 2. Openings 14 are positioned at the end of recesses 26 and openings 20 are positioned at the end of recesses 28. The shape of the recesses 26, 28 is generally the same in this embodiment. Each recess 26, 28 extends from an opening 14, 20 to a surface adjacent the mounting surface 24. The recesses 26, 28 define an opening in the surface adjacent the mounting surface 24. In this embodiment, the cutting block 2 is intended to engage two mounting projections at the same time. Thus, openings 12, 14, 16 and 18, 20, 22 are provided in pairs. In order to allow two mounting projections to be guided simultaneously towards the openings, the recesses 26 and 28 follow a generally straight path and are parallel to each other, extending in a perpendicular direction from the respective surface adjacent the mounting surface 24.

Referring again to FIGS. 1 and 6, the width of the recesses 26, 28 increases towards the surface adjacent the mounting surface 24. In this embodiment the width increases at a constant rate to define a funnel shaped end 30, 32 to each recess 26, 28.

Figure 3:
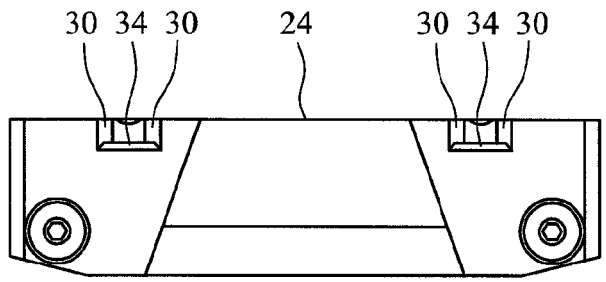
FIG. 3 is a top view of the embodiment of FIG. 1.
Figure 4:
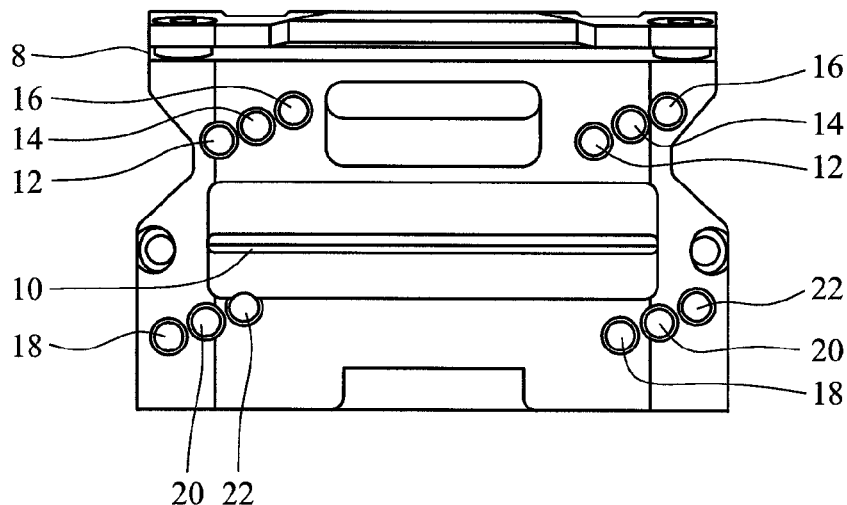
FIG. 4 is a front view of the embodiment of FIG. 1.

As can be seen in FIGS. 1 and 3, the depth of the recesses 26 also increases towards the surface adjacent the mounting surface 24. This is provided by chamfered section 34.

In use, a surgeon can align mounting projections with the pairs of openings 14, 20 by using the recesses 26, 28. The process will be described with reference to FIGS. 9a-9d, which are diagrammatic representations of the installation of the cutting block 2 on mounting projections 50 extending from a condyle of a knee joint. In FIGS. 9a-9d the cutting block is depicted in simplified form, showing only those features used to install the cutting block on the mounting projections, other features such as cutting slots are omitted to allow the method to be understood more clearly.

Figure 2:
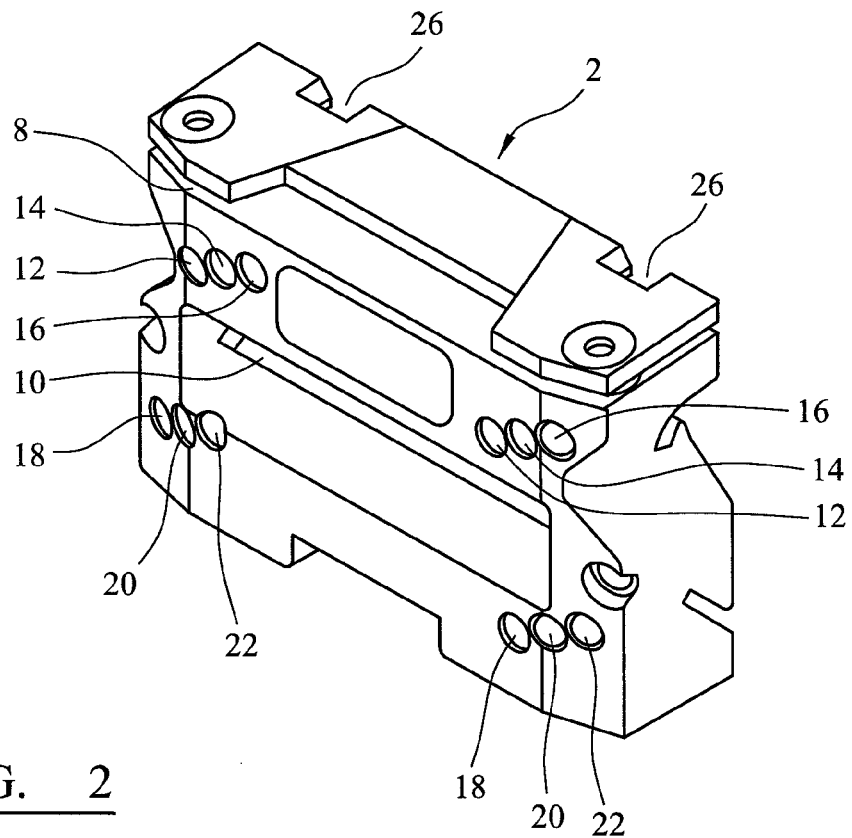
FIG. 2 is an isometric view from the front of the embodiment of FIG. 1.
Figure 9A:
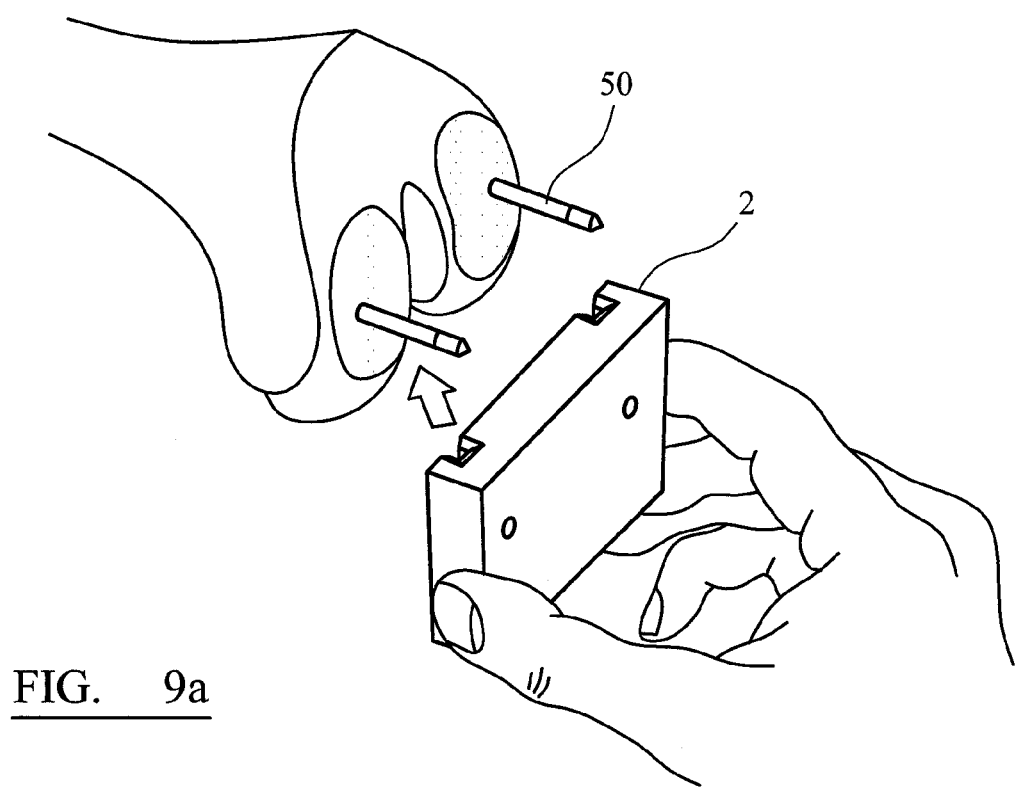
FIGS. 9a-9d are a diagrammatic representation depicting the use of the embodiment of FIG. 1 to engage mounting projections during knee surgery.
Figure 9B:
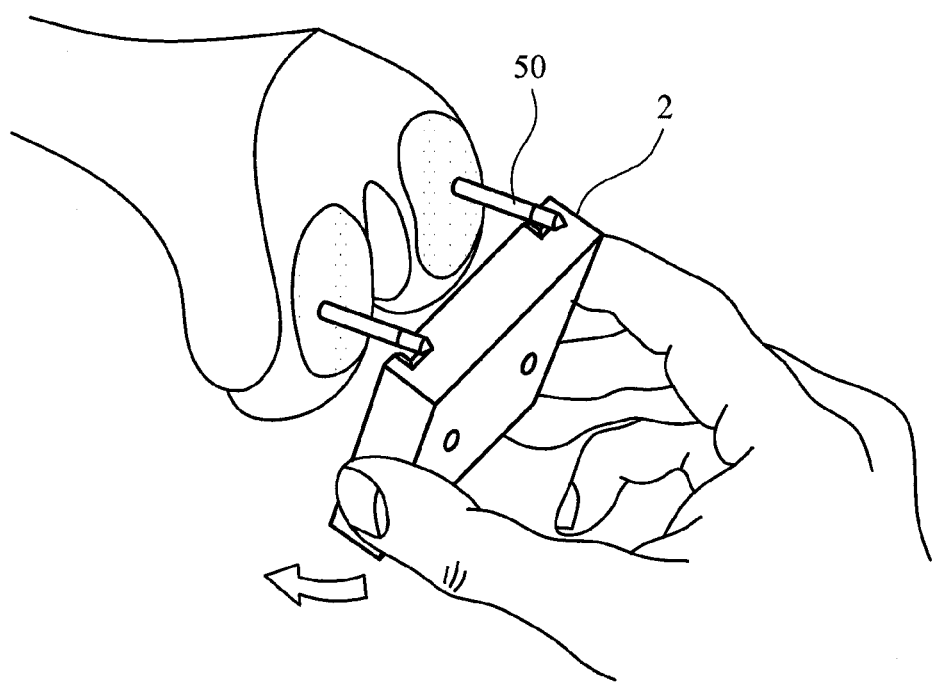
Figure 9C:
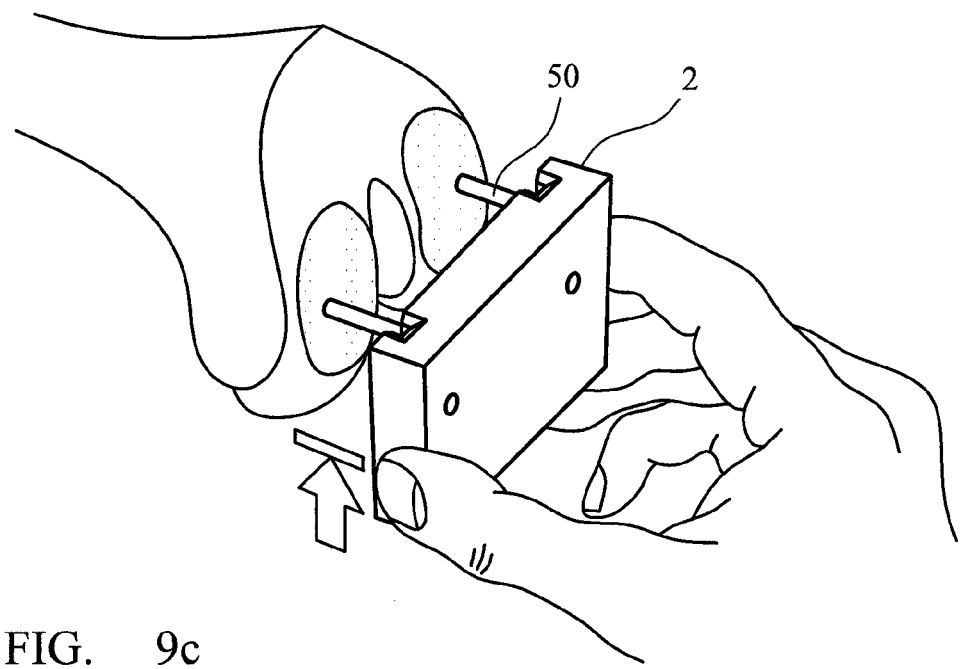

The surgeon will typically install the cutting block 2 so that the mounting surface 24 is hidden from view and the surgeon is looking at the cutting block from a position similar to that illustrated in FIG. 2. Although the location of the openings on the mounting surface 24 cannot be seen, the recesses 26, 28 extend into adjacent surfaces and can be identified by the surgeon. As depicted in FIG. 9a, the surgeon can then align the mounting projections with the recesses 26, 28. The cutting block 2 is then tilted slightly and used to locate the mounting projections 50 in the end of the recesses 26, 28 (FIG. 9b). Next, the cutting block 2 is slid so that the mounting projections 50 travel along the recesses 26, 28 and are guided towards the openings 14, 20 (FIG. 9c).

The increasing width sections 30, 32 and increasing depth section 34 assists the surgeon in aligning the cutting block 2 on the mounting projections if the mounting projections have not been installed at precisely the required distance apart. These features enable the cutting block to align the mounting projections 50 more accurately as they are slid along the recesses 26, 28.

Figure 9D:
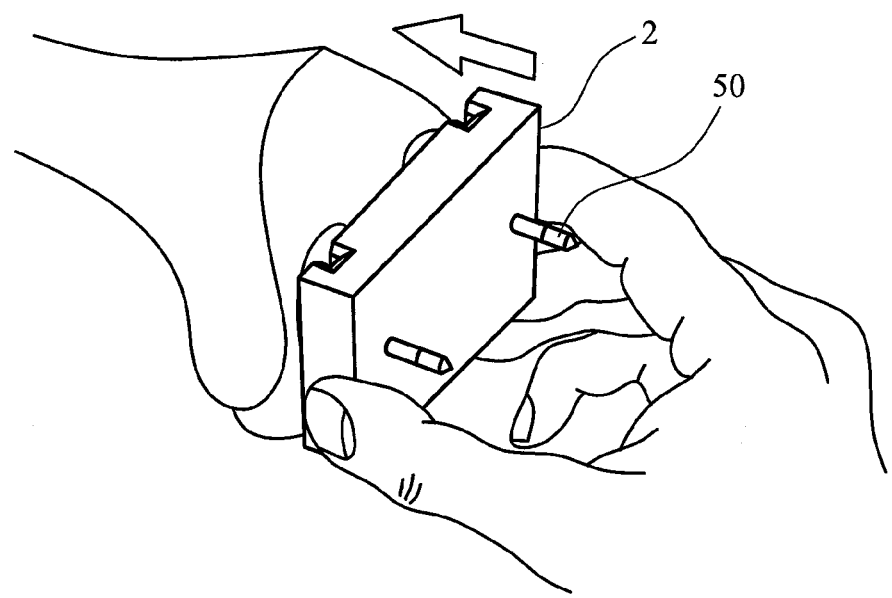

Once the mounting projections 50 reach the end of the recesses 26, 28 the surgeon can simply push the cutting block 2 onto the mounting projections knowing that they are already partially received within the openings (FIG. 9d).

This embodiment illustrates how not all the openings 12, 14, 16 and 18, 20, 22 need be provided with recesses to assist insertion of mounting projections. Design constraints may mean that providing a recess for each opening is not possible because it weakens the structure or because the recesses cannot be formed so close together. However, in the embodiment of the present invention the recesses are chosen to be positioned next to the pairs of openings 14, 20 which are most often used in surgery. For example, provided that the mounting projections are correctly positioned in a patient, openings 14 and 20 are used in the majority of surgical procedures so the recess assists the surgeon align mounting projections with the most commonly used openings.

It will be appreciated that the precise design and profile of the recesses may be varied depending on the requirements for a particular surgical instrument. In this embodiment the recess has a width generally equal to the width of an opening. However, the width may also be narrower than the opening, particularly when the mounting projections may have rounded rather than square ends in the direction of the openings. Likewise, it may be desirable to vary the depth of the recess so that it is shallower immediately adjacent the opening. This allows the opening to retain as much depth as possible which can be important for ensuring a secure attachment to the mounting projections.

This embodiment also illustrates how the recesses can be intersected by other surface features of the mounting surface 24. For example, recesses 28 are intersected by cutting slot 6.

In an alternate embodiment (not illustrated), which is the same as the FIG. 1 embodiment, except as described below, more pairs of openings may be provided with recesses. In this embodiment, for example all of openings 12, 14, 16 may be provided with a recess extending from them. The recesses for each pair of openings may extend at different angles relative to others of the recesses to assist in differentiating between the opening each recess leads to. It could also enable the recesses to move further apart from each other towards the side surface than adjacent the openings. Optionally, the recesses may be labelled on the side surface to further assist identification. The label may be laser marked on the side surface.

Figure 8:
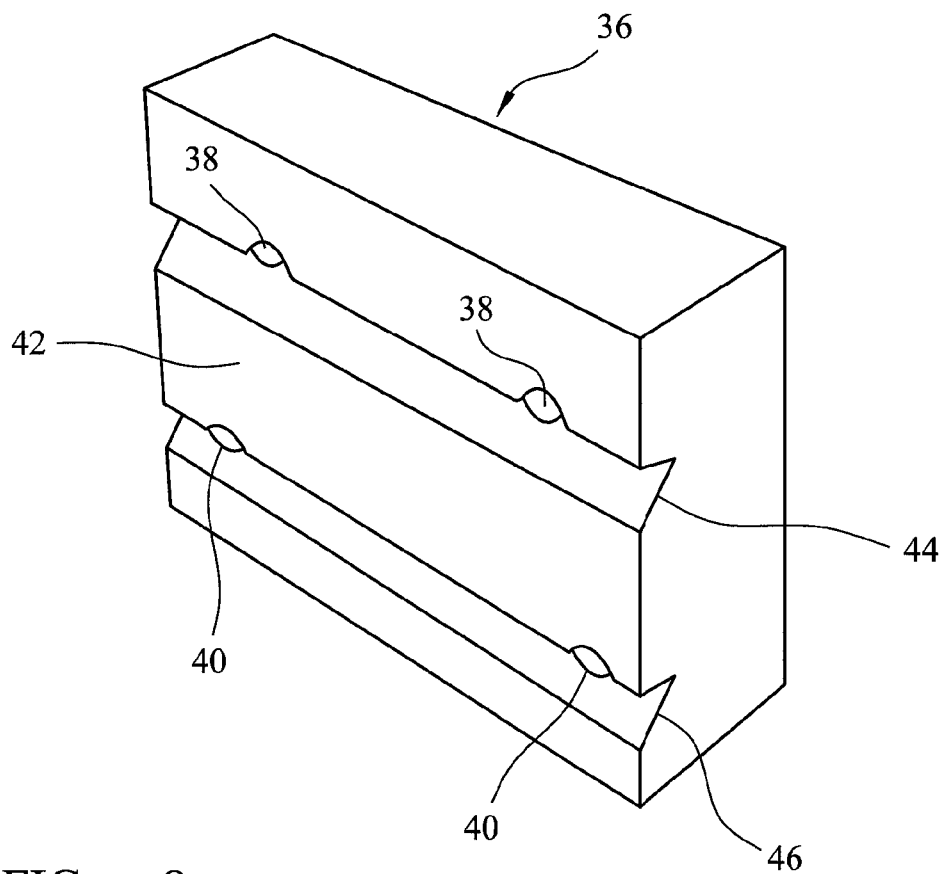
FIG. 8 is a diagrammatic representation of a second embodiment according to the present invention.

Another embodiment of the present invention is depicted in perspective view in FIG. 8. In this embodiment a cutting block 36 is provided with two pairs of openings 38, 40. Each pair of openings 38, 40 have a respective recess 44, 46. The recesses 44, 46 extend across the entirety of the mounting surface 42 so that they are visible from two opposite sides adjacent the mounting surface. Recess 44 extends past both openings 38 and recess 46 extends past both openings 40. The recesses 44, 46 may have a centre line which is offset from the line joining the centres of the openings 38 or openings 46 (as depicted in FIG. 8). Alternatively, in other embodiments, the centre line of the recesses may be coincident with the line joining the centres of the openings.

Figure 10A:
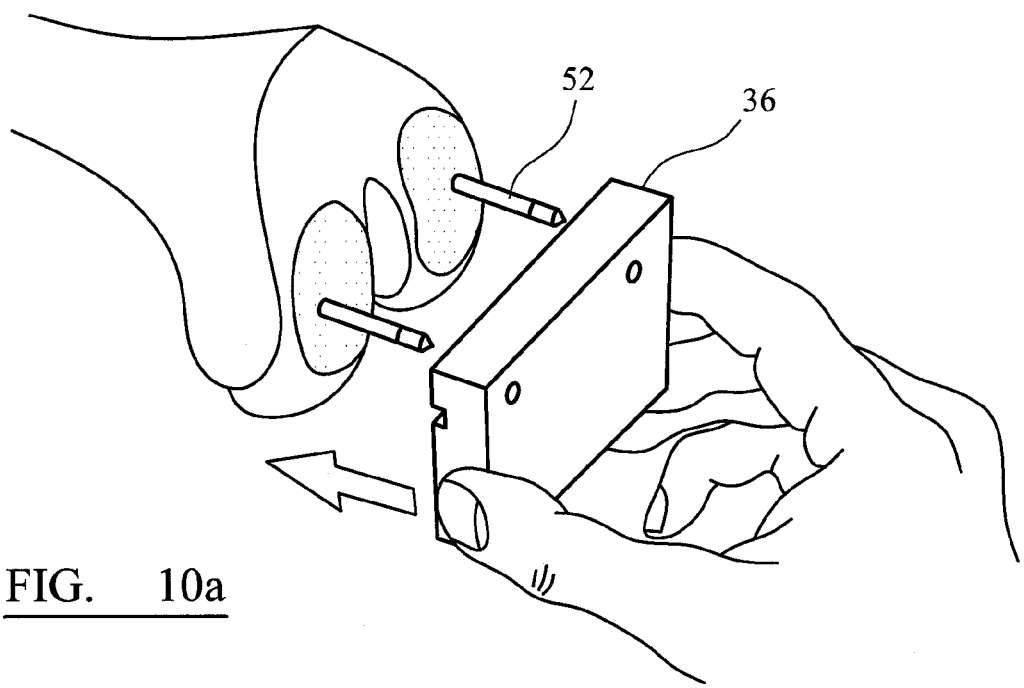
FIGS. 10a-10d are a diagrammatic representation depicting the use of the embodiment of FIG. 8 to engage mounting projections during knee surgery.
Figure 10B:
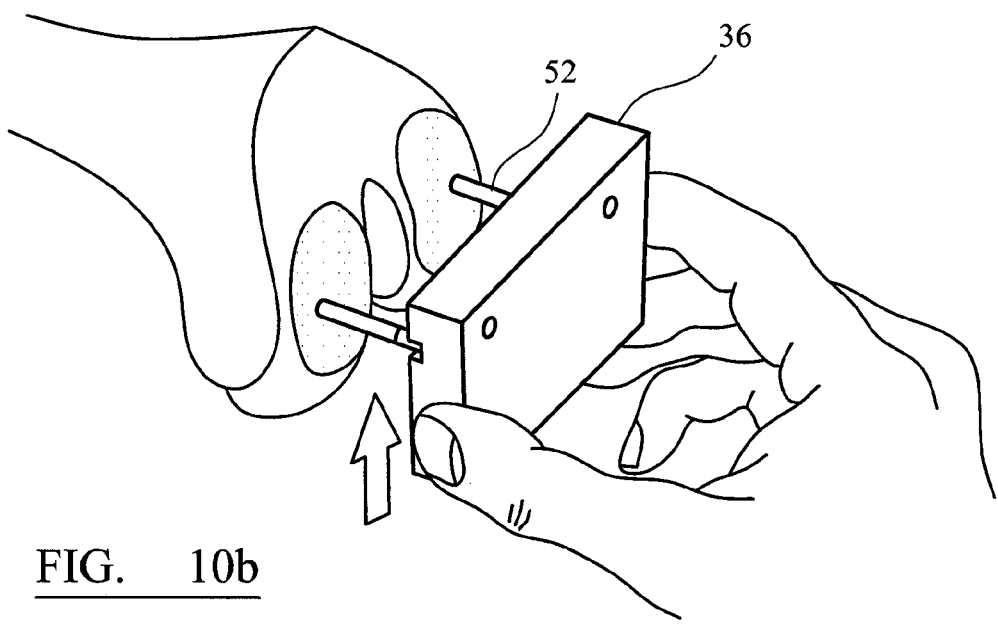
Figure 10C:
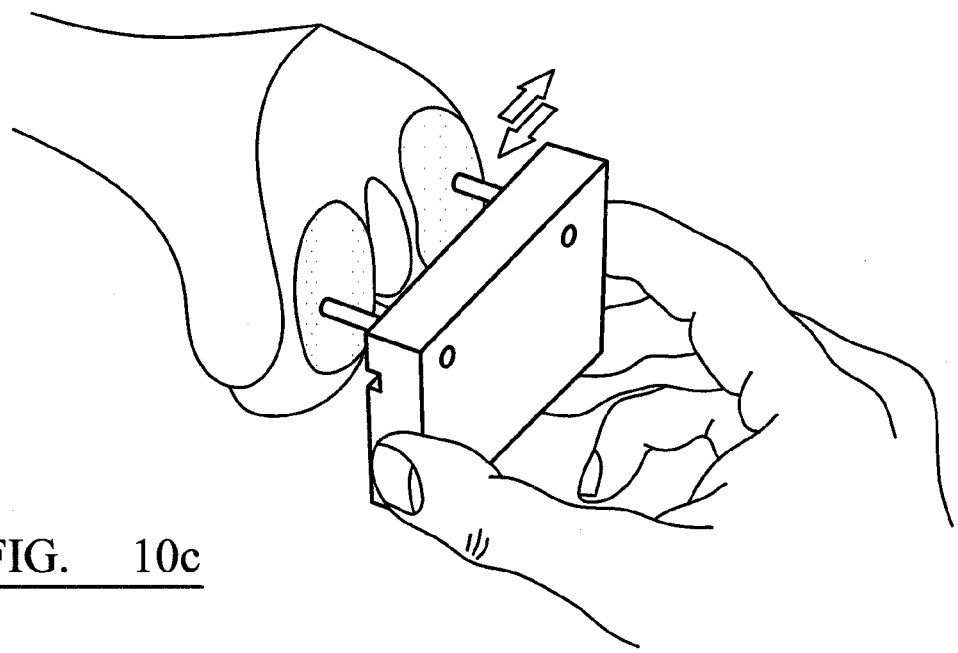
Figure 10D:
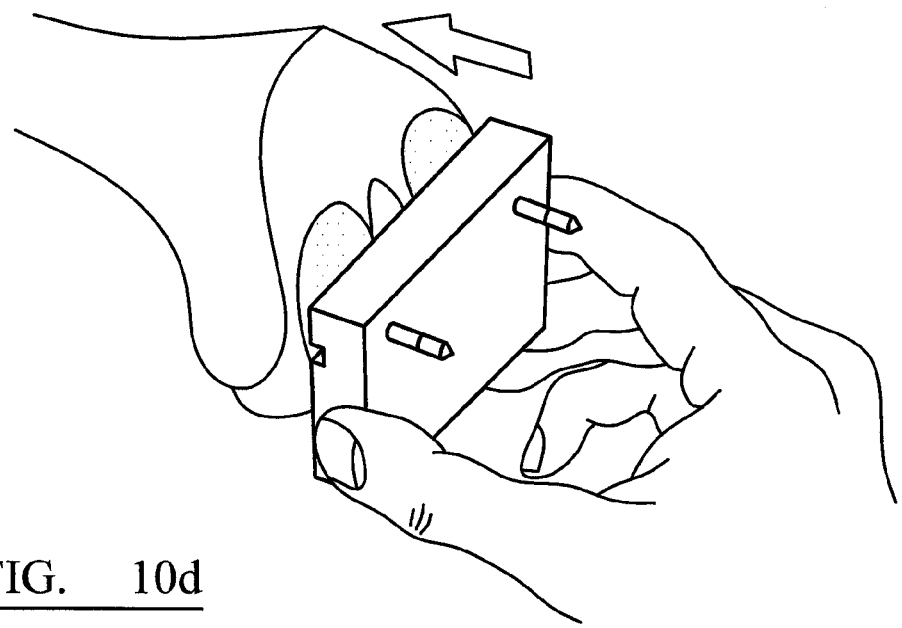

The process of using this embodiment will now be described with reference to FIGS. 10a-10d, which are diagrammatic representations of the installation of the cutting block 36 on mounting projections 52 extending from a condyle of a knee joint. In FIGS. 10a-10d the cutting block is depicted in simplified form, showing only those features used to install the on the mounting projections, other features such as cutting slots are omitted to allow the method to be understood more clearly. In use, the surgeon may place the cutting block 36 so that the projections 52 are against the mounting surface 42 (FIG. 10a). and the cutting block 36 is then moved until both projections 52 engage somewhere along the length of the recess 44 (FIG. 10b). This can be assisted because the surgeon can gauge the position of the recess 44, 46 by viewing the side adjacent the mounting surface. Once the mounting projections are engaged with recess 44 or 46 the surgeon can then use the recess to guide the projections into the openings 38 or 40. The cutting block 36 is slid sideways until the mounting projections 52 engage the openings 38 or 40 (FIG. 10c) and then pushed on the mounting projections 52 (FIG. 10d).

The engagement of the openings with the mounting projections can provide tactile feedback to the surgeon. This tactile feedback is enhanced when the openings are offset from the recess and have a chamfered lead-in, as depicted in FIG. 8.

In an alternate method of use, a surgeon aligns one of the mounting projections with recess 44, 46 as appropriate. The mounting projection is then slid along recess 44 or 46 past the first of the openings 38, 40 until the second projection is aligned with the recess 44, 46. The surgeon then aligns the second projection with the recess and continues sliding the cutting block 42 until the mounting projections are aligned with the openings 38 or 40.

All of the above described embodiments may be manufactured from any suitable material, for example a medical grade metal or metal alloy.

The features of the embodiments may be combined. For example, the pairs of parallel recesses discussed in the embodiments of FIG. 1 may be combined with the single recess for two openings in the embodiment of FIG. 8. Likewise, the present invention can be applied to any number of mounting projections. Although the embodiments described are for aligning a cutting block with a pair of projections, the invention is equally as useful with other surgical instruments or when a surgical instrument is mounted on one, two, three or more mounting projections.

The invention claimed is:

1. A surgical instrument system for use with a bone, comprising:
    a mounting projection adapted for insertion into the bone; and
    a cutting block comprising a mounting surface, wherein the mounting surface has at least one opening for receiving the mounting projection and a recess that communicates with the at least one opening and extends linearly from the at least one opening;
wherein:
    the cutting block has a first surface adjacent to the mounting surface, a second surface adjacent to the mounting surface and spaced from the first surface, a surface opposite the mounting surface, a width between the first surface and the second surface and a depth between the mounting surface and the opposite surface;
    the cutting block also has an elongate cutting guide slot extending through the entire depth of the cutting block for guiding resection of the bone;
    the cutting guide slot extends in a direction different from the direction of the recess in the mounting surface;
    the recess is a blind recess that extends from the at least one opening to one of the first and second surfaces and is sized so as to act as a track to guide the mounting projection to the at least one opening;
    the recess has an end between the first and second surfaces; and
    the at least one opening is positioned at the end of the recess.

2. The surgical instrument system of claim 1, wherein the recess does not extend through the entire depth of the cutting block.

3. The surgical instrument system of claim 1, wherein the cutting block is placed on the mounting projection after the mounting projection has been inserted into the bone.

4. The surgical instrument system of claim 2, wherein the recess extends to a first edge of the mounting surface such that the recess extends into the first surface, and wherein the recess is generally straight and substantially perpendicular to the first edge of the mounting surface.

5. The surgical instrument system of claim 4, wherein the recess has a width that increases in the direction towards the first surface.

6. The surgical instrument system of claim 4, wherein the recess has a depth that increases in the direction towards the first surface.

7. The surgical instrument system of claim 6, wherein the recess flares outwardly at a junction with the first surface.

8. The surgical instrument system of claim 1, wherein the mounting surface defines a plane and has a first opening and a second opening, each opening sized to accept a mounting projection; wherein a first recess extends from the first opening and a second recess extends from the second opening; wherein both the first and second recesses extend to a first edge of the mounting surface such that both the first and second recesses extend into the first surface; and wherein the first and second recesses are substantially parallel to each other in the plane of the mounting surface.

9. The surgical instrument system of claim 1, wherein the mounting surface has at least one further opening sized to receive a mounting projection and wherein no recess extends from the at least one further opening.

10. The surgical instrument system of claim 1, wherein the cutting block has a plurality of elongate cutting guide slots extending through the entire depth of the cutting block.

11. A surgical cutting block, comprising:
a mounting surface that has a first opening and a second opening, each sized to receive a mounting projection;
a first surface adjacent to the mounting surface and a second surface adjacent to the mounting surface, the cutting block having a width extending between the first and second surfaces and a depth extending from the mounting surface;
a plurality of elongate cutting guide slots extending through the entire depth of the cutting block from the mounting surface;
wherein the mounting surface has a first recess that does not extend the entire depth or the entire width of the cutting block, the first recess extending linearly from an end at the first opening and a second recess that does not extend the entire depth or the entire width of the cutting block, the second recess extending linearly from an end at the second opening, the first and second recesses being substantially parallel to each other in the plane of the mounting surface; and wherein both the first recess and the second recess extend to opposite ends at a first edge of the mounting surface such that both the first recess and the second recess extend into the first surface adjacent to the mounting surface.

12. The surgical cutting block of claim 11, wherein at least one of the first recess and the second recess has a width that increases in the direction towards the first surface.

13. The surgical cutting block of claim 11, wherein at least one of the first recess and the second recess has a depth that increases in the direction towards the first surface.

14. The surgical cutting block of claim 11, wherein at least one of the first recess and the second recess is generally straight and substantially perpendicular to the first edge of the mounting surface.

15. The surgical cutting block of claim 11, wherein the mounting surface has at least one further opening sized to receive a mounting projection and wherein no recess extends from the at least one further opening.

16. A surgical cutting block, comprising:
a mounting surface that has at least one opening for receiving a mounting projection, a first surface adjacent to the mounting surface, a second surface adjacent to the mounting surface, a width extending between the first and second surfaces, a depth extending from the mounting surface, a plurality of elongate cutting guide slots extending through the entire depth of the cutting block from the mounting surface, and a recess that does not extend through the entire width or depth of the cutting block, the recess extending linearly from an end at the at least one opening to a first edge of the mounting surface such that the recess extends into the first surface; and
wherein the recess has a width that increases in the direction towards the first surface.

17. The surgical cutting block of claim 16, wherein the recess has a depth that increases in the direction towards the first surface.

18. The surgical cutting block of claim 16, wherein the recess is generally straight and substantially perpendicular to the first edge of the mounting surface.

19. The surgical cutting block of claim 17, wherein the mounting surface has at least one further opening sized to receive a mounting projection and wherein no recess extends from the at least one further opening.

20. The surgical cutting block of claim 17, wherein each cutting guide slot extends in a different direction than the recess.

* * * * *